United States Patent [19]

Kirstein et al.

[11] Patent Number: 5,576,438
[45] Date of Patent: Nov. 19, 1996

[54] ISOSERINE DERIVATIVES AND THEIR USE AS LEUKOTRIENE ANTAGONISTS

[75] Inventors: Dorte Kirstein, Lyngby; Schneur Rachlin, Værløse, both of Denmark

[73] Assignee: Leo Pharmaceutical Products Ltd. A/S (Løvens Kemiske Fabrik Produktionsaktiesel Skab), Ballerup, Denmark

[21] Appl. No.: 335,860

[22] PCT Filed: Aug. 5, 1993

[86] PCT No.: PCT/DK93/00254

§ 371 Date: Jan. 3, 1995

§ 102(e) Date: Jan. 3, 1995

[87] PCT Pub. No.: WO94/02338

PCT Pub. Date: Feb. 17, 1994

[30] Foreign Application Priority Data

Aug. 7, 1992 [GB] United Kingdom .................. 9216768

[51] Int. Cl.⁶ .................... C07D 215/06; C07D 215/18
[52] U.S. Cl. ............................. 546/476; 546/180
[58] Field of Search ..................... 546/176, 180

[56] References Cited

U.S. PATENT DOCUMENTS

| | | | |
|---|---|---|---|
| 4,918,081 | 4/1990 | Huang et al. | 514/311 |
| 4,962,203 | 10/1990 | Young et al. | 546/180 |
| 5,102,881 | 4/1992 | Zamboni et al. | 514/228.2 |

FOREIGN PATENT DOCUMENTS 206751 12/1986 European Pat. Off. .
9103466 3/1991 WIPO .

OTHER PUBLICATIONS

DeLima, Eur J Pharmacol, 213(1), pp. 63–70, 1992, Medline abstract 92362769.
Griffiths, Proc Natl Acad Aci USA, 92(2), pp. 517–521, 1995, Medline abstract 95132631.
Naclerio, Respir Dis, 143(5pt2), pp. S91–S95, 1991, Medline abstract 91206770.
Nasser, Thorax, 49(8), pp. 743–748, 1994, Medline abstract 94378107.
Jolly, Pharmacology, 38(6), pp. 352–362, 1989, Medline abstract 90047032.
Rice, Biophys Res Commun, 124(1), pp. 303–307, 1984, Medline abstract 85046512.
Furstenberger, Carcinogenesis, 15(12), pp. 2823–2827, 1994, Medline abstract 95094385.

Primary Examiner—C. Warren Ivy
Assistant Examiner—D. Margaret M. Mach
Attorney, Agent, or Firm—Cushman Darby & Cushman, LLP

[57] ABSTRACT

The present invention relates to hitherto unknown compounds of formula; Y stands for —CH=CH—; $R_1$ is hydrogen or halogen, preferably fluorine, chlorine or bromine; $R_2$ is halogen, preferably fluorine, chlorine or bromine, $CH_3$, $OCH_3$, $NO_2$ or $CF_3$, and n=0–3, preferably 0, 1 or 2; A stands for an acidic group, e.g. carboxy, 1-H-tetrazolyl or a hydroxamic acid group. The present compounds are of value in the human and veterinary practice as lipoxygenase inhibitors and/or leukotriene antagonists.

5 Claims, No Drawings

ISOSERINE DERIVATIVES AND THEIR USE AS LEUKOTRIENE ANTAGONISTS

This application is a 371 of PCT/DK93/00254, filed 5 Aug. 1993.

The present invention relates to hitherto unknown compounds useful in the human and veterinary therapy, to pharmaceutically acceptable salts thereof, to bioreversible derivatives thereof, to methods for producing said new compounds, to pharmaceutical compositions containing the new compounds, to dosage units of the compositions, and to methods of treating patients using said compositions and dosage units.

Leukotrienes, which are formed via the 5-lipoxygenase pathway of arachidonic acid metabolism, are implicated in a variety of pathophysiologic functions, such as bronchoconstriction, plasma exudation, coronary artery spasm, leukocyte chemotaxis and neutrophil degranulation[1]. It is therefore of considerable interest to develop compounds which inhibit 5-lipoxygenases and thereby the production of leukotrienes, or antagonize the effects of leukotrienes.

[1] P. J. Piper and M. N. Sumhoun, Br. Med. Bull. 43(1987), 297.

International patent application No. PCT/DK90/00201 describes a series of quinolyl methoxy substituted N-phenyl substituted isoserine (i.e. 3-amino-2-hydroxypropionic acid) derivatives with good leukotriene antagonistic activity.

Now it has surprisingly turned out that replacement of the —$CH_2O$-group with —CH=CH— (trans) and concomitant substitution with halogen in the quinoline ring provides compounds with even more potent leukotriene antagonistic activity, especially in the presence of human serum albumin.

The present compounds have the general formula I

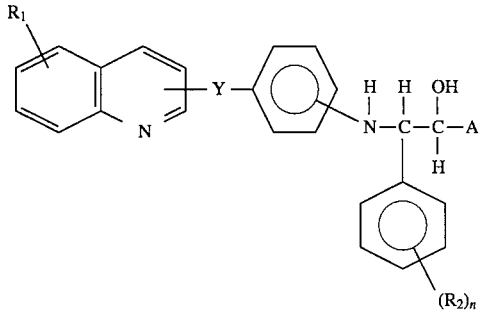

Y stands for —CH=CH—;

$R_1$ is hydrogen or halogen, preferably fluorine, chlorine or bromine;

$R_2$ is halogen, preferably fluorine, chlorine or bromine, $C_3$, $OCH_3$, $NO_2$ or $CF_3$, and n=0–3, preferably 0, 1 or 2;

A stands for an acidic group, e.g. carboxy, 1-H-tetrazolyl or a hydroxamic acid group.

Among the preferred compounds of the invention are those of formula I, in which A stands for a carboxy group.

The compounds described herein contain more centers of asymmetry and may thus give rise to diastereoisomers and optical isomers. The present invention is meant to comprehend such possible diastereoisomers as well as their racemic and resolved optically active forms.

The present salts of the compounds of formula I may be formed with pharmaceutically acceptable inorganic or organic acids, such as hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, and maleic acid.

The present salts of the compounds of formula I may also be formed with pharmaceutically acceptable, inorganic or organic bases. As examples of salts formed with pharmaceutically acceptable, non-toxic bases, mention may be made of alkali metal salts and alkaline earth metal salts, such as lithium, sodium, potassium, magnesium, calcium salts, as well as salts with ammonia and suitable non-toxic amines, such as $C_1$–$C_6$-alkylamines, e.g. triethylamine, $C_1$–$C_6$ alkanolamines, e.g. diethanolamine or triethanolamine, procaine, cycloalkylamines, e.g. dicyclohexylamine, benzylamines, e.g. N-methylbenzylamine, N-ethylbenzylamine, N-benzyl-β-phenethylamine, N,N'-dibenzylethylenediamine or dibenzylamine, and heterocyclic amines, e.g. morpholine, N-ethylpiperidine and the like.

Even if the present compounds are well absorbed after enteral administration, in some cases it can be advantageous to prepare suitable bioreversible derivatives of compounds of the invention, i.e. to prepare so-called prodrugs, preferably derivatives, the physiochemical properties of which leads to improved solubility at physiological pH and/or absorption of the compound in question.

Such derivatives are for instance esters of N-hydroxymethyl derivatives of compounds of the invention, such compounds being prepared by reaction of a secondary amine-function of compounds of the invention with formaldehyde[2,3,4,5] followed by reaction with a suitable acidic compound or activated derivatives of such compounds, for instance with bisulfite[6], N,N-dimethylglycine, N,N-diethyl-β-alanine, or phosphoric acid[7], but other suitable acids which form bioreversible derivatives with desirable physicochemical properties can be used as well.

[2] R. G. Kallen and W. P. Jencks, J. Biol. Chem. 241 (1966) 5864.
[3] C. J. Martin and M. A. Marini, J. Biol. Chem. 242 (1967) 5736.
[4] M. Levy and D. E. Silberman, J. Biol. Chem. 118 (1937) 723.
[5] S. Lewin and D. A. Humphany, J. Chem. Soc. B (1966) 210.
[6] B. C. Jain, B. H. Iyer, and P. C. Guha, Science and Culture 11 (1946) 568.
[7] S. A. Varia, S. Schuller, K. B. Sloan and V. J. Stella, J. Pharm. Sci., 73 (1985) 1068 and following papers.

Further examples include esters formed with the acidic function in the molecule, such as simple esters, e.g. methyl or ethyl, acyloxyalkyl, alkoxycarbonyloxyalkyl or aminoacyloxyalkyl esters, which are readily hydrolyzed in vivo or in vitro.

Among the above esters the following are preferred: alkanoyloxymethyl with from 3 to 8 carbon atoms, 1-(alkanoyloxy)ethyl with from 4 to 9 carbon atoms, alkoxycarbonyloxymethyl with from 3 to 6 carbon atoms, 1-(alkoxycarbonyloxy)ethyl with from 4 to 7 carbon atoms, and α-aminoalkanoyloxymethyl with from 2 to 6 carbon atoms.

Other preferred esters are lactonyl esters, e.g. 3-phthalidyl, 4-crotonolactonyl or γ-butyrolacton-4-yl esters.

Also within the scope of the invention are methoxymethyl, cyanomethyl, or mono- or dialkyl substituted aminoalkyl esters, e.g. 3-dimethylaminoethyl, 2-diethylaminoethyl, or 3-dimethylaminopropyl esters.

In particular, such esters are preferred which are well absorbed upon enteral administration and during or after the absorption are hydrolysed to the compounds of formula I.

Other suitable methods to improve the physicochemical properties and solubility of the compounds concerned can be used as well.

Metabolites of arachidonic acid include prostaglandins and leukotrienes. Both of these two groups of metabolites are important in the pathophysiology of inflammatory and allergic reactions. Many inhibitors of prostaglandin synthesis are being used as anti-inflammatory agents[8], but relatively few leukotriene inhibitors are presently clinically acceptable. The first step in the biochemical synthesis of all leukotrienes is the peroxidation at the 5-carbon atom of arachidonic acid. This reaction is catalyzed by the enzyme 5-lipoxygenase, present mainly in leukocytes. Leukotriene $B_4$ is one of the most potent chemoattractants for polymorphonuclear leukocytes, and at the same time causes aggregation and degranulation of these inflammatory cells. It is thus a potent pro-inflammatory hormone. Leukotriene $C_4$, $D_4$, and $E_4$ together comprise the agent known previously as "slow-reacting substance of anaphylaxis" (SRS-A), which is three orders of magnitude more potent than histamine in causing bronchoconstriction, and also regulates microvascular smooth muscle contractility and permeability. It is therefore a mediator of asthmatic, allergic and inflammatory reactions.

[8] R. J. Flower, S. Moncada and J. R. Vane, in: The Pharmacological Basis of Therapeutics (1980), ed. A. G. Gilman, L.S. Goodmann and A. Gilman, (Macmillan, New York) p. 682.

Inhibition of 5-1-lipoxygenase thus leads to a decrease in the formation of all of these inflammatory and allergic mediators. This has very important clinical implications, as specific 5-lipoxygenase inhibitors and leukotriene antagonists are of potential interest in the therapy of asthma, allergy, rheumatoid arthritis, spondyloarthritis, gout, atherosclerosis, proliferative and inflammatory skin disorders, such as psoriasis and atopic dermatitis, chronic inflammatory bowel disease, and other inflammatory conditions, vasospasm associated with angina pectoris, pulmonary hypertension, cystic fibrosis, the adult respiratory distress syndrome, ischemic and reperfusion injury etc.[9]. The identification of specific 5-lipoxygenase inhibitors and leukotriene antagonists is thus a novel approach with very wide implications for the treatment of a diversity of clinical disorders.

[9] E. J. Goetzl, D. G. Payan and D. W. Godman, J. Clin. Immunol. 4 (1984) 79.

Leukotriene biosynthesis inhibitors may be identified using rat peritoneal leukocytes labelled with [1-$^{14}$C]arachidonate and stimulated with the calcium ionophore A23187[10]. Compounds produced according to the examples 1–5 were observed to inhibit the formation of leukotriene $B_4$ at an assay concentration of 10 µM.

[10] I. Ahnfelt-Rønne, D. Kirstein and C. Kærgaard-Nielsen, European J. Pharmacol. 155 (1988) 117.

Leukotriene antagonists may be identified by observing the contractions elicited in preparations of guinea-pig ileum strips suspended in a physiological buffer by addition of pure leukotriene $D_4$ ($LTD_4$)[10]. The ileum strips are connected to an isogonic transducer, and the contractions are continuously recorded on a multichannel recorder. Before addition of $LTD_4$, atropine and indomethacin are added to the buffer in order to block any cholinergic or prostaglandin mediated contractile effects. Test compounds to be studied with respect to leukotriene antagonism are dissolved in DMSO and added to the organ bath 2 minutes prior to addition of $LTD_4$ at $10^{-9}$M (final concentration), the final concentration of DMSO being 0.1%, a concentration which can be shown not to affect the ileum response to $LTD_4$. The test compounds may be added at various concentrations.

[10] I. Ahnfelt-Rønne, D. Kirstein and C. Kærgaard-Nielsen, European J. Pharmacol. 155 (1988) 117.

When the compounds of the present invention were added to the ileum preparation before addition of $LTD_4$ a significant inhibition occurred of the specific $LTD_4$-induced contraction. This inhibition occurred at concentrations as low as 0.1–1 nM. On the other hand, contractions induced with histamine at $10^{-7}$ M were not inhibited by these compounds even at micromolar concentrations.

It is of importance to investigate the receptor binding properties of leukotriene antagonists in relation to their inhibition of smooth muscle contraction. Receptor binding studies may be performed with guinea-pig lung membranes in a direct competition assay between a leukotriene antagonist and [$^3$H]$LTD_4$ for binding to the $LTD_4$ receptor [10,11]. A $pIC_{50}$ value is determined as the negative logarithm of the molar concentration of antagonist inhibiting [$^3$H]$LTD_4$ binding by 50%. $pIC_{50}$ values for the compounds according to the Examples 6 and 17 were found to be 8.7 and 8.2, and 8.6 and 7.7, respectively in the absence and presence of 0.1% human serum albumin. These values indicate that the affinities of the compounds for the $LTD_4$ receptor are very high, also in the presence of albumin.

[10] I. Ahnfelt-Rønne, D. Kirstein and C. Kærgaard-Nielsen, European J. Pharmacol. 155 (1988) 117.
[11] S. Mong, H.-L. Wu, M. O. Scott, M. A. Lewis, M. A. Clarke, B. M. Welchman, C. M. Kinzig, J. G. Gleason and S. T. Crooke, J. Pharmacol. Exp. Ther. 234 (1985) 316.

The present invention also relates to a method for producing the present compounds.

In one embodiment, an amine of the formula II

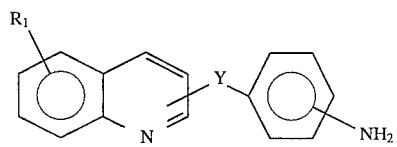

in which $R_1$, Y, and n have the above meanings, is reacted with a compound of the formula III

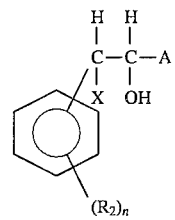

in which $R_2$, A and n have the above meanings, and X is capable of forming a "good leaving group", X thus standing for e.g. a halogen atom, such as chlorine, bromine or iodine, or an alkyl- or arylsulphonyloxy group, but other leaving groups can be used as well, such as an alkylsulphate group, a chlorosulphonyloxy group, an alkylsulphite group, a mono- or dialkylphosphate group or a nitrate group, to form a compound of the formula I.

During the reaction A may be protected with conventional protecting groups for instance in the case of a carboxyl group as an ester.

The reaction is performed in a suitable inert organic solvent, such as dimethylformamid, but other solvents can be used as well. The reaction is preferably performed at ambient temperature, but in some cases it is convenient to cool the reaction mixture below room temperature, or to heat the reaction mixture above room temperature, up to the boiling point of the solvent used, depending on the nature of the reactants of the formulae II and III used. The crude reaction products of the formula I are collected by filtration, or, after dilution with water, extracted from the reaction mixture with a suitable solvent, such as diethyl ether, ethyl acetate, dichloromethane or chloroform. The products are purified. e.g. by recrystallization or by chromatography.

In another embodiment, an amine of the formula II is reacted with a compound of the formula IV

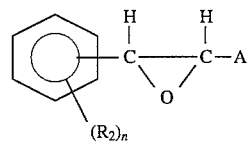

in which $R_2$, A and n have the above meanings.

The reaction is performed either in a suitable inert organic solvent, such as methanol, ethanol, dimethylformamide or hexamethyl phosphoric triamide, or in water, or in mixtures thereof. The reaction is performed at a temperature about or above room temperature, up to the boiling point of the solvent used. In some cases it can, however, be convenient to cool the reaction mixture below room temperature, depending on the nature of the compound of the formula IV used. The isolation and purification of the products can be performed as described above.

Additionally, the acidic functionalities A can be prepared according to the following general reactions schemes from compounds of formula I in which A is CN or COOH:

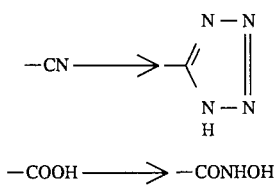

The present compounds are intended for use in pharmaceutical compositions which are useful in the treatment of the above mentioned diseases.

The amount required of a compound of formula (I) (hereinafter referred to as the active ingredient) for therapeutic effect will, of course, vary both with the particular compound, the route of administration and the mammal under treatment. A suitable dose of a compound of formula (I) for systemic treatment is 0.1 to 20 mg per kilogram bodyweight, the most preferred dosage being 0.2 to 10 mg/kg of mammal bodyweight, administered one or more times daily.

In spray formulations, an anti-asthmatic dose of a compound of formula (I) may be from 1 µg to 5 mg of compound per kilogram bodyweight, a preferred dosage range being 1 µg to 0.5 mg/kg of mammal bodyweight.

While it is possible for an active ingredient to be administered alone as the pure chemical, it is preferable to present it as a pharmaceutical formulation. Conveniently, the active ingredient comprises from 0.1% to 100% by weight of the formulation. Conveniently, dosage units of a formulation contain between 0.07 mg and 1 g of the active ingredient. For topical administration, the active ingredient preferably comprises from 1% to 2% by weight of the formulation but the active ingredient may comprise as much as 10% w/w. Formulations suitable for nasal or buccal administration, (such self-propelling powder-dispensing formulations described hereinafter), may comprise 0.1 to 20% w/w, for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefor and optionally other therapeutic ingredient(s). The carrier(s) must be "acceptable" in the sense of being compatible with the other ingredients of the formulations and not deleterious to the recipient thereof.

The formulations include those in a form suitable for oral, ophthalmic, rectal, parenteral (including subcutaneous, intramuscular and intravenous), transdermal, intra-articular, topical, nasal, or buccal administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredient. Compressed tablets may be prepared by compressing, in a suitable machine, the active ingredient in a free-flowing form, such as a powder or granules, optionally mixed with a binder, lubricant, inert diluent, surface active or dispersing agent. Moulded tablets may be made by moulding, in a suitable machine, a mixture of the powdered active ingredient and a suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration include liquid or semi-liquid preparations, such as liniments, lotions, oil-in-water or water-in-oil emulsions, such as creams, ointments or pastes; or solutions or suspensions, such as drops. For example, for ophthalmic administration, the active ingredient may be presented in the form of aqueous eye drops as, for example, a 0.1–1.0% solution.

Formulations suitable for administration to the nose or buccal cavity include powder, self-propelling and spray formulations, such as aerosols and atomizers. The formulations, when dispersed, preferably have a particle size in the range of 10 to 100µ.

Such formulations are most preferably in the form of a finely comminuted powder for pulmonary administration from a powder inhalation device or self-propelling powder-dispensing formulations, where the active ingredient, as a finely comminuted powder, may comprise up to 99.9% w/w of the formulation. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$–$C_6$-alkyl hydrocarbons or halogenated $C_1$–$C_6$-alkyl hydrocarbons or mixtures thereof; chlorinated and flourinated $C_1$–$C_6$-alkyl hydrocarbons are especially preferred. Generally, the propellant constitutes 50 to 99.9% w/w of the formulation whilst the active ingredient constitutes 0.1 to 20% w/w, for example about 2% w/w, of the formulation.

The pharmaceutically acceptable carrier in such self-propelling formulations may include other constituents in addition to the propellant, in particular a surfactant or a solid diluent or both. Surfactants are desirable since they prevent agglomeration of the particles of active ingredient and maintain the active ingredient in suspension. Especially valuable are liquid non-ionic surfactants and solid anionic surfactants or mixtures thereof. Suitable liquid non-ionic surfactants are esters and partial esters of fatty acids with aliphatic polyhydric alcohols, for instance, sorbitan monooleate and sorbitan trioleate, known commercially as "Span 80" (Trade Name) and "Span 85" (Trade Name), respectively. The liquid non-ionic surfactant may constitute from 0.01 up to 20% w/w of the formulation, though preferably it constitutes below 1% w/w of the formulation. Suitable solid anionic surfactants include alkali metal, ammonium and amine salts of dialkyl sulphosuccinate (where the alkyl groups have 4 to 12 carbon atoms). The solid anionic surfactants may constitute from 0.01 up to 20% w/w of the formulation, though preferably below 1% w/w of the composition solid diluents may be advantageously incorporated in such self-propelling formulation where the density of the active ingredient differs substantially from the density of the propellant; also, they help to maintain the active ingredient in suspension. The solid diluent is in the form of a fine powder, preferably having a particle size of the same order as that of the particles of the active ingredient. Suitable solid diluents include sodium chloride, sodium sulphate and sugars.

Formulations of the present invention may also be in the form of a self-propelling formulation wherein the active ingredient is present as such in suspension or in solution. Such self-propelling formulations may comprise the active ingredient, propellant and co-solvent, and advantageously an anti-oxidant stabiliser. The propellant is one or more of these already cited above. Co-solvents are chosen for their solubility in propellant, their ability to dissolve the active ingredient, and for their having the lowest boiling point consistent with these above-mentioned properties. Suitable co-solvents are $C_1$–$C_6$-alkyl alcohols and ethers and mixtures thereof. The co-solvent may constitute 5 to 40% w/w of the formulation, though preferably less than 20% w/w of the formulation. Antioxidant stabilisers may be incorporated in such solutions-formulations to inhibit deterioration of the active ingredient and are conveniently alkali metal ascorbates or bisulphites. They are preferably present in an amount of up to 0.25% w/w of the formulation.

Such self-propelling formulations may be prepared by any method known in the art. For example, the active ingredient (either as particles as defined hereinbefore as such or in suspension in a suitable liquid or in up to 20% w/v solution in an acceptable co-solvent, as appropriate) is mixed with any other constituents of a pharmaceutically acceptable carrier. The resulting mixture is cooled, introduced into a suitable cooled container, and propellant is added thereto in liquid form; and the container is sealed. Alternatively, such self-propelling formulations may be prepared by mixing the active ingredient either in particles as hereinbefore defined or in 2 to 20% w/v alcohol or aqueous solution as appropriate, together with the remaining constituents of the pharmaceutically acceptable carrier other than the propellant; introducing the resulting mixture, optionally with some propellant, into a suitable container; and injecting the propellant, under pressure, into the container at ambient temperature through a valve which comprises a part of the container and is used to control release of the formulation from it. Desirably, the container is purged by removing air from it at a convenient stage in the preparation of the self-propelling formulation.

A suitable container for a self-propelling formulation is one provided with a manually-operable valve and constructed of aluminium, stainless steel or reinforced glass. The valve should, of course, be one having the desired spray characteristics of particle size as hereinbefore defined. Advantageously, the valve is of the type which delivers a fixed amount of the formulation on the occasion of each operation of the valve, for example, about 50 to 100 microliters of formulation in each delivery.

Formulations of the present invention may also be in the form of an aqueous or dilute alcoholic solution, optionally a sterile solution of the active ingredient for use in a nebuliser or atomizer, wherein an accelerated air stream is used to produce a fine mist consisting of small droplets of the solution. A buffering agent and a surface active agent may also be included in such a formulation which should also contain a preservative such as methylhydroxybenzoate.

Other formulations suitable for nasal administration include a fine powder having a particle size of 10 to 100 microns which is administered in the manner in which snuff is taken, i.e. by rapid inhalation through the nasal passage from a container of the powder held close up to the nose.

In addition to the aforementioned ingredients, the formulations of this invention may include one or more additional ingredients, such as diluents, buffers, flavouring agents, binders, surface active agents, thickeners, lubricants, preservatives, e.g. methylhydroxybenzoate (including anti-oxidants), emulsifying agents and the like.

The compositions may further contain other therapeutically active compounds usually applied in the treatment of the above mentioned pathological conditions, for instance glucocorticoids, anti-histamines, platelet activating factor (PAF) antagonists, anticholinergic agents, methyl xanthines, β-adrenergic agents, salicylates, indomethacin, flufenamate, naproxen, timegadine, gold salts, penicillamine, serum cholesterol-reducing agents, retinoids, zinc salts, and salicylazosulfapyridin (Salazopyrin).

According to the invention, the present compounds are administered to a patient suffering from one of the above mentioned pathological conditions in a daily dose (for adults) from 0.2 mg to 7000 mg, preferably from 1–3500 mg, and in the veterinary practice correspondingly in daily doses from 0.5 to 100 mg/kg bodyweight.

The invention will now be further described in the following Examples:

EXAMPLE 1

E-(2R,3 R;2S,3S)-3-phenyl-N-3-[2-(7-chloroquinolyl)-2-ethenyl]-phenyl isoserine ethyl ester A mixture of E-3-[2-(7-chlorocquinolyl)-2-ethenyl]-aniline (2.8 g, 10 mmol) and (±)trans-3-phenyloxirane-2- carboxylic acid ethyl ester (2.0 ml, 11 mmol) in ethanol (75 ml) is refluxed for 24 hours. After cooling, the resulting precipitate is collected by filtration, and washed with ethanol and ether.

The title compound is obtained with a melting point of 161°–163° C.

EXAMPLE 2

E-(2R,3R;2S,3S)-3-phenyl-N-3-[2-(quinolyl)-2-ethenyl]-phenyl isoserine ethyl ester By following the procedure of Example 1, but replacing E-3-[2-(7-chloroquinolyl)-2-ethenyl]aniline with E-3-[2-(quinolyl)-2-ethenyl]aniline, the title compound is obtained. It is isolated as the hydrochloride with a melting point of 132°–138° C.

EXAMPLES 3–5

By following the procedure of Example 1 and using the appropriate starting materials, compounds of Table 1 are obtained as E-racemates (2R,3R;2S,3S)

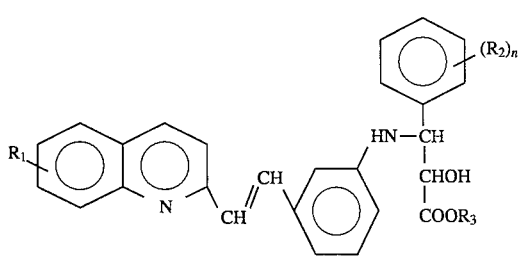

TABLE 1

| Ex. No. | $R_1$ | —$(R_2)_n$ | $R_3$ | Melting point |
|---|---|---|---|---|
| 3 | 7-Cl— | 4-Cl— | —$C_2H_5$ | 180–182° C. |
| 4 | 7-Cl— | 4-$CH_3O$— | —$CH_3$ | 134–136° C. |
| 5 | H— | 2-$CH_3$—<br>4-$CH_3$— | —$C_2H_5$ | 154–155° C. |

EXAMPLE 6

E-(2R,3R;2S,3S)-N-3-[2-(7-chloroquinolyl)-2-ethenyl]-phenyl-3-phenyl isoserine, sodium salt To a solution of ethyl ester (Example 1) (1.4 g, 3 mmol) in ethanol (40 ml) was added 2N NaOH (2 ml). The solution was refluxed for 1½ hours. After cooling, the resulting precipitate was collected by filtration, and washed with cold water and ether.

The title compound was obtained as a dihydrate.

Melting point: >250° C.

EXAMPLES 7–12

By following the procedure of Example 6 and using the appropriate starting materials, compounds of Table 2 are obtained as racemates (2R,3R;2S,3S)

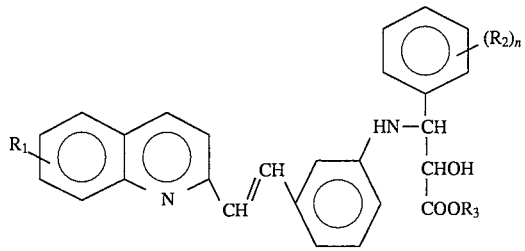

TABLE 2

| Ex. No. | $R_1$ | —$(R_2)_n$ | $R_3$ | Melting point |
|---|---|---|---|---|
| 7 | H— | 4-$CH_3$— | Na— | 168–210° C. |
| 8 | H— | 2-$CH_3$—, 4-$CH_3$— | H— | 205–206° C. |
| 9 | H— | 4-F— | Na— | 185–250° C. |
| 10 | 7-Cl— | 4-Cl— | Na— | 183–195° C. |
| 11 | H— | 4-$CH_3O$— | Na— | 172–184° C. |
| 12 | 7-Cl— | 4-$CH_3O$— | Na— | 160–250° C. |

EXAMPLE 13

E-(2R,3R;2S,3S)-3-(2,3-difluorophenyl-N-3-[(2-(quinolyl)-2-ethenyl]-phenyl isoserine To a solution of E-3-[2-(quinolyl)-2-ethenyl]-aniline (0.5 g, 2 mmol) in ethanol (10 ml) is added a solution of (±)-E-3-(2,3-difluorophenyl)oxirane-2-carboxylic acid sodium salt (0.56 g, 2.5 mmol) in water (2.0 ml) and ethanol (3.0 ml). The reaction mixture is refluxed for 24 hours. After cooling to room temperature, the precipitate is filtered off and the impure sodium salt is obtained. The sodium salt is dissolved in water (10 ml) and pH adjusted to pH≡6.0 by adding 3N acetic acid.

The precipitate was filtered off, washed with water and the title compound is obtained, with. a melting point of 233°–235° C.

EXAMPLE 14

E-(2R,3R;2S,3S)-N-3-[2-(7-chloroquinolyl)-2-ethenyl]-phenyl-3-(2,6-difluorophenyl) isoserine By following the procedure of Example 13, but replacing E-3-[(2-quinolinyl)-2-ethenyl]-aniline with E-3-[2-(7-chloroquinolinyl)-2-ethenyl]-aniline and (±)-E-3-(2,3-difluorophenyl)oxirane-2-carboxylic acid sodium salt with 3-(2,6-difluorophenyl)oxirane-2-carboxylic acid sodium salt, the title compound is obtained with a melting point: 215°–217° C.

EXAMPLE 15

E-(2R,3R;2S,3S)-N-3-[2-(7-chloroquinolyl)-2-ethenyl]-phenyl-3-(2,5-difluorophenyl) isoserine By following the procedure of Example 13, but replacing E-3-[(2-quinolinyl)-2-ethenyl]-aniline with E-3-[2-(7-chloroquinolinyl)-2-ethenyl]-aniline and (±)-E-3-(2,3-difluorophenyl)oxirane-2-carboxylic acid sodium salt with 3-(2,5-difluorophenyl)oxirane-2-carboxylic acid sodium salt, the title compound is obtained with a melting point: 196°–198° C.

EXAMPLE 16

E-(2R,3R;2S,3S)-N-3-[2-(7-chloroquinolyl)-2-ethenyl]-phenyl-3-(4-trifluoromethylphenyl) isoserine, sodium salt By following the procedure of Example 13, but replacing E-3-[(2-quinolinyl)-2-ethenyl]-aniline with E-3-[2-(7-chloroquinolinyl)-2-ethenyl]-aniline and (±)-E-3-(2,3-difluorophenyl)oxirane-2-carboxylic acid sodium salt with 3-(4-trifluoromethylphenyl)oxirane-2-carboxylic acid sodium salt, the title compound is obtained. It is isolated as a sodium salt with a melting point: >250° C.

EXAMPLE 17

E-(2R,3R;2S,3S)-3-phenyl-N-3-[(2-quinolyl)-2-ethenyl]-phenyl isoserine, sodium salt To a solution of the ethyl ester of Example 2, and by following the procedure of Example 6, the title compound is obtained.

$^1$H NMR (CD$_3$)$_2$SO: δ=3.83 (1H, d), 4.50 (1H, d), 6.50 (1H, bd), 6.85 (2H, m), 7.02 (1H, t), 7.10–7.32 (4H, m), 7.43 (2H, d), 7.54 (1H, m), 7.62 (1H, d, J=16.3 Hz), 7.74 (1H, dr), 7.82 (1H, d), 7.93 (1H, bd), 7.99 (1H, bd), 8.32 (1H, d).

EXAMPLE 18

E-(−)-(2S,3S)-N-3-[2-(7-chloroquinolyl)-2-ethenyl]-phenyl-3-phenyl isoserine, sodium salt By following the procedure of Example 14, but replacing (±)trans-3-(2,6-difluorophenyl)oxirane-2-carboxylic acid, sodium salt with (−)-(2R,3S)-3-phenyloxirane-2-carboxylic acid, sodium salt, the title compound is obtained.

Melting point: >250° C.
$[α]_D^{25}$=+24.0 (c=1, MeOH).
$[α]_D^{25}$=−90.4 (c=1, 1n HCl).

EXAMPLE 19

E-(+)-(2R,3R)-N-3-[2-(7-chloroquinolyl)-2-ethenyl]-phenyl-3-phenyl isoserine, sodium salt By following the procedure of Example 14, but replacing (±)trans-3-(2,6-difluorophenyl)oxirane-2-carboxylic acid, sodium salt with (+)-(2S,3R)-3-phenyloxirane-2-carboxylic acid, sodium salt, the title compound is obtained.

Melting point: >250° C.
$[α]_D^{25}$=−23.7 (c=1, MeOH).
$[α]_D^{25}$=+90.1 c=1, 1n HCl).

EXAMPLE 20

E-(2R,3R;2S,3S)-N-[2-(7-chloroquinoly)-2-ethenyl]-phenyl-3-(4-nitrophenyl) isoserine, ethyl ester By following the procedure of Example 1, but replacing (±)trans-3-phenyloxirane-2-carboxylic acid ethyl ester with (±)trans-3-(4-nitrophenyl)oxirane-2-carboxylic acid ethyl ester, the title compound is obtained with a melting point of 175°–177° C.

EXAMPLE 21

E-(2R,3R;2S,3S)-N-[2-(7-chloroquinolyl)-2-ethenyl]-phenyl-3-(4-nitrophenyl) isoserine, sodium salt By following the procedure of Example 6, but replacing E-3-[(2-quinolinyl)-2-ethenyl]-aniline with E-3-[2-(7-chloroquinolinyl)-2-ethenyl]-aniline and E-3-(2,3-difluorophenyl)oxirane-2-carboxylic acid sodium salt with 3-(4-nitrophenyl)oxirane-2-carboxylic acid sodium salt, the title compound is obtained. It is isolated as a sodium salt with a melting point: >250° C.

EXAMPLE 22

Aerosol

| | |
|---|---|
| E-(−)-(2S,3S)-N-3-[2-(7-chloroquinolyl)-2-ethenyl]-phenyl-3-phenyl isoserine, sodium salt (the active substance) | 1000 mg |
| Sorbitan trioleate | 700 mg |
| Monofluorotrichloromethane | 595 g |
| Difluorodichloromethane | 798 g |

The active substance is micronized in a jet-mill. The majority of the particles should be less than 5 μm in diameter.

A drug concentrate is prepared by dissolving sorbitan trioleate in a small amount of monofluorotrichloromethane and adding the active substance. The concentrate is homogenized carefully. The concentrate is transferred to a sealed tank provided with a refrigeration system. The remaining propellants are added under stirring and cooling to −50° C.

Suitable aerosol container are filled with the calculated amount of formulation and sealed immediately with metering valves with suitable actuators. Each puff delivers 50 μg of the active substance.

EXAMPLE 23

Tablet

| | |
|---|---|
| E-(−)-(2S,3S)-N-3-[2-(7-chloroquinolyl)-2-ethenyl]-phenyl-3-phenyl isoserine, sodium salt (active substance) | 100 mg |
| Lactose | 75 mg |
| Starch | 12 mg |
| Methyl cellulose | 2 mg |
| Sodium carboxymethyl cellulose (CMC—Na) | 10 mg |
| Magnesium stearate | 1 mg |

The active substance, lactose and starch are mixed to a homogeneous state in a suitable mixer and moistened with a 5 percent aqueous solution of methylcellulose 15 cps. The mixing is continued until granules are formed. If necessary, the wet granulation is passed through a suitable screen and dried to a water content of less than 1% in a suitable dryer, e.g. fluid bed or drying oven. The dried granulaton is passed through a 1 mm screen and mixed to a homogeneous state with CMC—Na. Magnesium stearate is added, and the mixing is continued for a short period of time.

Tablets with a weight of 200 mg are produced from the granulation by means of a suitable tabletting machine.

EXAMPLE 24

Formulation for injection

| | |
|---|---|
| E-(−)-(2S,3S)-N-3-[2-(7-chloroquinolyl)-2-ethenyl]-phenyl-3-phenyl isoserine, sodium salt (active substance) | 1% |
| Sodium chloride | q.s. |
| Water for injection to make | 100% |

The active substance is dissolved in water for injection. The solution is made isotonic with sodium chloride. The solution is filled into ampoules and sterilized.

What we claim is:

1. A compound selected from the group consisting of compounds of the formula I

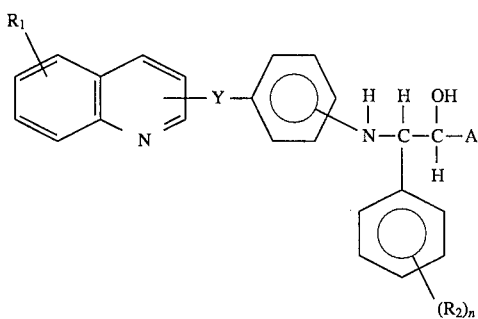

in which Y stands for —CH=CH—; $R_1$ is hydrogen or halogen; $R_2$ is halogen, $CH_3$, $OCH_3$, $NO_2$ or $CF_3$, and n=0–3; A stands for carboxy, 1-H-tetrazolyl or a hydroxamic acid group; pharmaceutically acceptable, non-toxic salts thereof or in-vivo hydrolysable esters thereof.

2. A salt according to claim 1, in which the salt is selected from the group consisting of salts formed with hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, and maleic acid, alkali metal salts, alkaline earth metal salts, salts with ammonia and salts with non-toxic amines.

3. A compound of claim 1 which is selected from the group consisting of:
   E-(2R,3R;2S,3S)-3-phenyl-N-3-[2-(7-chloroquinolyl)-2-ethenyl]-phenyl isoserine;
   E-(2R,3R;2S,3S)-3-phenyl-N-3-[2-quinolyl)-2-ethenyl]-phenyl isoserine;
   E-(2R,3R;2S,3S)-N-3-[2-(7-chloroquinoiyl)-2-ethenyl]-phenyl-3-(2,6-difluorphenyl) isoserine;
   E-(2R,3R;2S,3S)-N-3-[2-(7-chloroquinolyl)-2-ethenyl]-phenyl-3-(2,5-difluorophenyl) isoserine;
   E-(2R,3R;2S,3S)-N-3-[2-(7-chloroquinolyl)-2-ethenyl]-phenyl-3-(4-methoxyphenyl) isoserine;
   E-(2R,3R;2S,3S)-N-3-[2-(7-chloroquinolyl)-2-ethenyl]-phenyl-3-(4-chlorophenyl) isoserine;
   E-(2R,3R;2S,3S)-3-(4-methoxyphenyl)-N-3-[(2-quinolyl)-2-ethenyl]-phenyl isoserine;
   or a salt or a pure enantiomeric form thereof.

4. A compound of claim 1 which is E-(−)-(2S,3S)-N-3-[2-(7-chloroquinolyl)-2-ethenyl]-phenyl-3-phenyl isoserine, sodium salt.

5. A pharmaceutical composition comprising a compound according to claim 1 and a pharmaceutically acceptable carrier.

* * * * *